(12) United States Patent
Johnson

(10) Patent No.: US 6,774,996 B2
(45) Date of Patent: Aug. 10, 2004

(54) MEASURING DENSITY VARIATIONS

(75) Inventor: John L. Johnson, Heidelberg (DE)

(73) Assignee: The United States of America as represented by the Secretary of the Army, Washington, DC (US)

( * ) Notice: Subject to any disclaimer, the term of this patent is extended or adjusted under 35 U.S.C. 154(b) by 241 days.

(21) Appl. No.: 10/171,570

(22) Filed: Jun. 11, 2002

(65) Prior Publication Data

US 2003/0227621 A1 Dec. 11, 2003

(51) Int. Cl.[7] .................................................. G01J 4/00
(52) U.S. Cl. ...................... 356/364; 356/436; 356/437; 359/495; 359/497
(58) Field of Search .................................. 356/364, 365, 356/128, 436, 437, 432, 445, 446; 359/495, 497, 494

(56) References Cited

U.S. PATENT DOCUMENTS

| | | | |
|---|---|---|---|
| 2,999,931 A | 9/1961 | Zingaro | 250/51.5 |
| 4,624,563 A | 11/1986 | Johnson | 356/152 |
| 4,626,100 A | 12/1986 | Johnson | 356/152 |
| 5,191,392 A | 3/1993 | Johnson | 356/353 |
| 5,404,222 A | 4/1995 | Lis | 356/349 |
| 5,610,704 A * | 3/1997 | Berzins et al. | 356/28.5 |
| 6,195,410 B1 | 2/2001 | Cash, Jr. | 378/43 |
| 6,348,998 B1 | 2/2002 | Johnson | 359/495 |

* cited by examiner

Primary Examiner—Frank G. Font
Assistant Examiner—Roy M. Punnoose
(74) Attorney, Agent, or Firm—Chang Hay Kyung; Dayn T. Beam

(57) ABSTRACT

A method and an apparatus for measuring the density variations, static and dynamic, in substances that are at least partially transparent to electromagnetic waves is disclosed. A special birefringement crystal phase shifting assembly encodes the angle of incidence resulting from the refractive effects of the electromagnetic waves having passed through a density variation. The angle of incidence is encoded as a poralization phase shift. Specifically, the poralization phase shift is between the ordinary and the extraordinary rays. That poralization phase shift has a known and definable relationship to the gas density experienced by the electromagnetic wave during its path.

24 Claims, 4 Drawing Sheets

MEASURING DENSITY VARIATIONS

DEDICATORY CLAUSE

The invention described herein may be manufactured, used and licensed by or for the Government for governmental purposes without the payment to me of any royalties thereon.

BACKGROUND OF THE INVENTION

Numerous methods and apparatuses are known for the purpose of measuring density and density variations in various substances. One group of this prior art employs visible light waves and their various properties such as phase shifts, interferometric fringe patterns, diffraction, and refraction. In another group, electromagnetic waves other than visible light (e.g., x-rays and infrared) have been used to make measurements of density. Prior art also teaches the use of a special birefringence crystal phase plate (phase shifting assembly) to encode the angle of incidence as a poralization phase shift. Prior art then uses the phase-shift-to-angle-of-incidence relationship to locate the position or source of an incoming electromagnetic wave. However, prior art does not teach, and does not make obvious, the application of this phase shifting assembly to encode as a poralization phase shift the change in the angle of incidence that would result from the refractive effects of density variations in a substance. This new use of the phase shifting plates establishes a known and definable relationship between poralization phase shifts and the density variations (i.e., density variation causes refraction, which causes a change in the angle of incidence, which is encoded as a poralization phase shift).

The use of a special phase shifting assembly to record an incoming angle of incidence and encode that angle of incidence as a poralization phase shift is well documented in U.S. Pat. No. 4,626,100 issued Dec. 2, 1986; U.S. Pat. No. 4,624,563 issued Nov. 25, 1986; U.S. Pat. No. 5,191,392 issued Mar. 2, 1993, and U.S. Pat. No. 6,348,998 issued Feb. 19, 2002. An important distinction between these special phase shifting assemblies and prior art is that these phase shifting assemblies measure the phase shift between the ordinary and extraordinary rays of a single wave. Prior art recognizes a phase shift from interference patterns or another related characteristic of light and requires at least two waves. Prior applications of these special phase shifting assemblies have been to locate the position of a source of light relative to the assembly, to generate a Fourier transform of the incident intensity image, and to generate high quality fringe patterns that vary in number with adjustments to a certain twist angle of the apparatus.

One objective of prior art is to adjust for the effects that density variations in gas have on the use of interferometric measurement methods. U.S. Pat. No. 5,404,222 issued Apr. 4, 1995, discloses and discusses a method of compensating for the refractive effects that turbulent gas has on interferometric measurements. All such prior art, including U.S. Pat. No. 5,404,222, appears dependent upon measuring the effects of the density variations by comparing two waves. Generally, one wave that passes through the varying density substance is compared with a second wave that has not passed through that substance to calculate the effects of the density variations. The differences in the two waves (e.g., path length or interference patterns caused by a phase shift) are then compared to determine the refractive index, which is then used to determine the density difference.

The concept of an X-ray interferometer was the subject of U.S. Pat. No. 2,999,931 issued Sep. 12, 1961 and U.S. Pat. No. 6,195,410 issued Feb. 27, 2001. In these patents the interference patterns created by the specific method or apparatus are used to obtain the desired information.

While the interference patterns discussed in the above references also can be used to determine the phase shift that created those patterns, measuring a phase shift between the ordinary and extraordinary rays of a single wave is not taught by the references other than those utilizing the phase shifting assembly. Therefore, prior art, individually and in combination, does not teach and does not make obvious the application of this phase shifting assembly to encode as a poralization phase shift the change in the angle of incidence that would result from the refractive effects of density variations in a substance.

The necessity of an unaffected or reference wave for comparison with the wave affected by the density varying substance is a requirement which may not be: available; timely available; or otherwise convenient in all situations. The need for real-time, accurate measurements of the density (static or dynamic) of a substance is an objective for which prior art cannot guarantee a workable or practical solution in all situations.

The method claims of this invention represent a unique combination of steps that is not taught, motivated or suggested by the prior art. The apparatus claims of this invention represent a unique combination of means and means plus structure that is not taught, motivated or suggested by the prior art. Certain apparatus claims include the use of a phase shifting assembly to perform the encoding means. Several different phase shifting assemblies have been noted in the references above. These claims represent a new use of those assemblies.

SUMMARY OF THE INVENTION

Described herein are a method and an apparatus for measuring the density variations, static and dynamic, in substances that are at least partially transparent to electromagnetic waves. A typical application would be to visually display the real-time variations in densities within a gas or liquid. A previously patented method using a special birefringement crystal phase shifting assembly encodes the angle of incidence resulting from the refractive effects of the electromagnetic waves having passed through a density variation. The angle of incidence is encoded as a poralization phase shift. Specifically, the poralization phase shift is between the ordinary and the extraordinary rays. That poralization phase shift has a known and definable relationship to the gas density experienced by the electromagnetic wave during its path.

Figure 1:
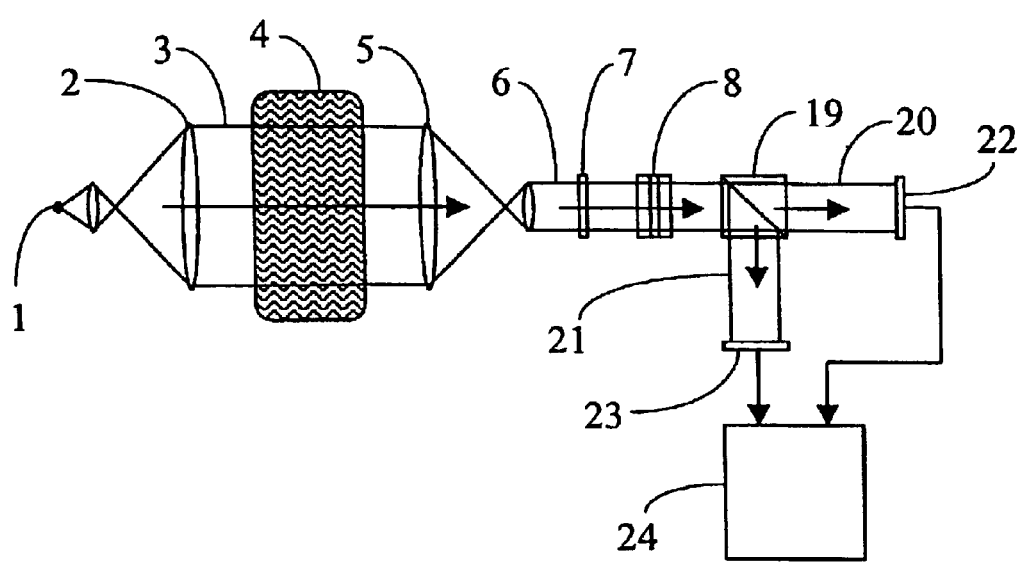
FIG. 1 is the preferred embodiment of the invention.

A separate block diagram of the method claims is not included as FIG. 1 may be readily used to understand the method claims.

DESCRIPTION OF THE PREFERRED EMBODIMENT

Referring now to the drawings wherein like numbers represent like parts, the following is the preferred embodiment of the invention.

The apparatus is shown in FIG. 1. A light source 1 is colliminated by an optical system 2, and the beam 3 is then transmitted through the desired region of gaseous turbulence 4. There, the density variations of the gas induce small spatial changes in the gas index of refraction which, in turn, cause small angular deviations of the colliminated light beam. The beam then passes through a second re-colliminating optical system 5 which reduces the beam diameter and also magnifies the angular deviations. Collimators 2 and 5 are realized, for example, by standard telescopes of either a refracting or reflecting type. The reduced beam 6 then passes through an initial linear polarizer 7 and then through a birefringent crystal assembly 8 called a phase shifting assembly.

Figure 2:
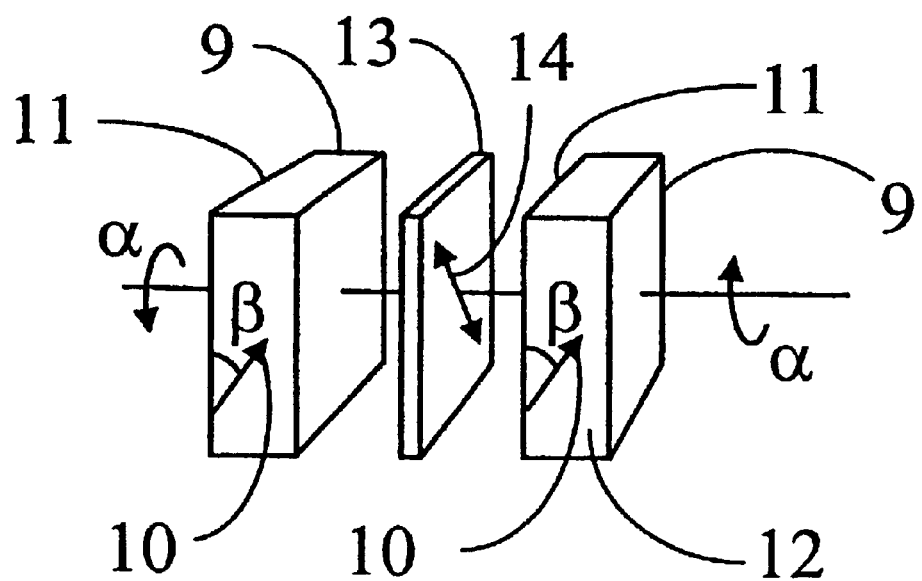
FIG. 2 is a more detailed view of the phase shifting assembly.
Figure 3:
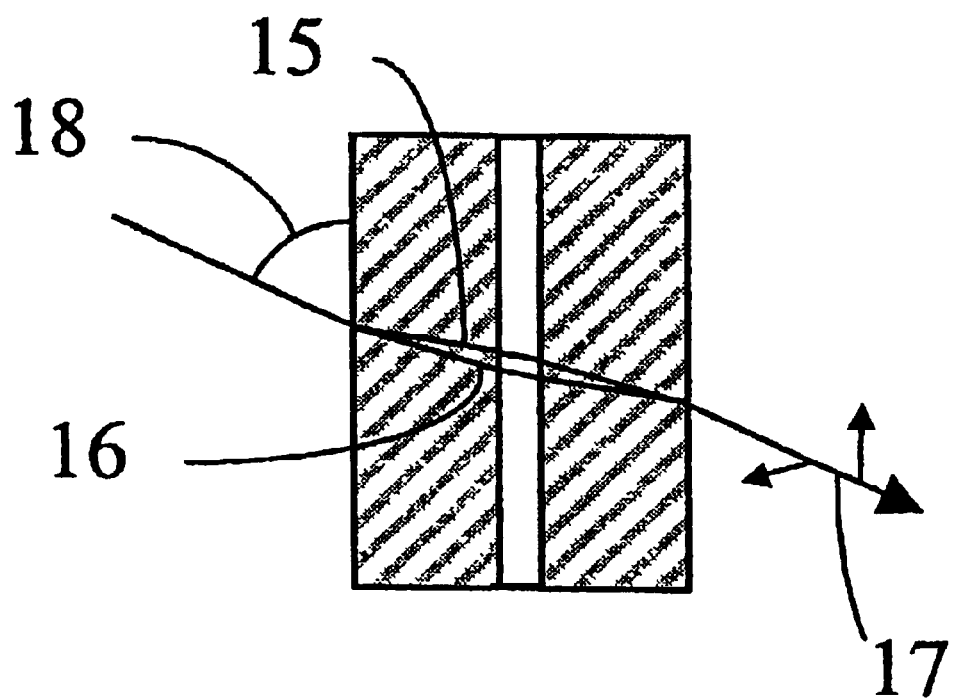
FIG. 3 is an isolated view of the light ray being phase shifted.

The particular construction of the phase shifting assembly used here is shown in FIG. 2 and consists of two plates 9 of birefringent crystal such as quartz or calcite cut with their crystal axes 10 at an angle $\beta$ to the plate surface 11. The plates are oriented so that the crystal axis of each plate lies initially in the same plane 12 and are parallel to each other. The two plates are then each rotated around the normal to their plate surfaces by an angle $\alpha$, each plate being given an equal and opposite rotation. This angle $\alpha$, called a twist angle, is usually only a few degrees in magnitude. Sandwiched between the birefringent plates is an achromatic half-wave plate 13 with an axis 14 that is oriented so as to interchange the ordinary ray 15 and the extraordinary ray 16. The result is a symmetric construction. For a twist angle $\alpha$ of zero the birefringent crystal assembly 8 would result in no overall effect on the ray of light passing through it. However, the use of a non-zero twist angle $\alpha$ introduces an asymmetry that generates a polarization shearing effect for angles of incidence in the plane of the original untwisted optical axes of the birefringent plates. The primary net effect is a relative phase shift between the polarization components of the incident light beam. In FIG. 3, the polarization phase shift 17 is a function of the angle of incidence 18 of the light ray passing through the assembly 8 and, in particular, for small angles, is directly proportional to the incident angle. This particular construction of the phase shifting assembly is more fully detailed in U.S. Pat. No. 6,348,998 issued Feb. 19, 2002, which is incorporated by reference.

Figure 4:
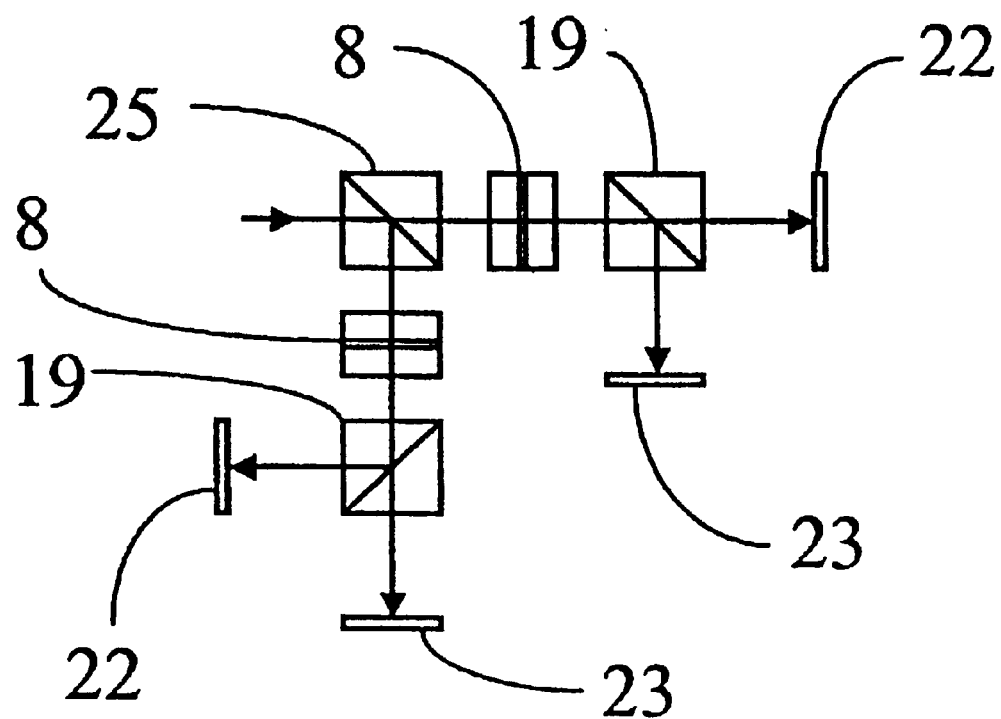
FIG. 4 is an alternate embodiment for a two-axis application.

The beam containing the encoded poralization phase shift then passes through a linear polarization analyzer 19 (e.g., a polarization beam splitter) positioned so as to divide the polarization components of the encoded beam into new components parallel 20 and normal 21 to the beam exiting the initial linear polarizer 7. These new components are each incident on a standard video camera detector array, which produces two intensity images $I_p$ (22) and $I_n$ (23) for the parallel and normal components, respectively. The angle of incidence at each point in the image is then computed pixel by pixel as a function of the difference divided by the sum of the two intensities at the corresponding pixel pairs of $I_p$ and $I_n$. This computation is displayed as the output image 24. This system provides full information about one component of the angle of incidence. For a system that simultaneously detects and displays full information about both components of the angle of incidence, an additional beam splitter 25 can be added immediately after the linear polarizer 7 and the remaining portion of the system would be replicated for each of the two separate beams exiting the beam splinter 25 as shown in FIG. 4.

Because the angular encoding and analyzing is done entirely by optical means, the images 22 and 23 are available in real time. By using a strobe light as the illumination source 1, the turbulence can be sampled at any strobe frequency, and the images 22 and 23 will still display the sampled data just as the human eye can observe strobe-illuminated high-speed phenomena. Further, the system can be used in other spectral regions by use of birefringent crystals and detector arrays effective in those spectral regions.

If a large-aperture phase shifting assembly is desired, it can be fabricated by tiling the desired aperture with many small, identical phase shifting assemblies.

The phase shifting effects of reflection and thin films on electromagnetic waves is well known in the art. The method and system described above can be employed to study the mechanical dynamics of reflecting surfaces as well as the density variations in thin films. Therefore, the use of the concept of "projecting the wave through a desired area of the substance" should be understood to include these applications. As an example, for a thin film the electromagnetic wave might pass into the film, reflect from an opposing boundary, and then pass out of the film.

It is anticipated that applications of this invention will range from the cosmic scale to quantum physics. In some applications the use of multiple systems will be obvious.

While it is anticipated that the steps and means of the claims will most often be performed by equipment or means known to those skilled in the art, all of these steps and means subsequent to the encoding step or means may be performed by the human body and brain. It is possible for the density variations to be viewed directly after the encoding step or means.

The individual steps and means described by the claims are well known to those skilled in the art and are taught by the prior art referenced. The uniqueness of the present invention is first in the unique use of the encoding step and means. This step and means encodes an angle of incidence change from the refractive effects of density variations as a poralization phase shift between the extraordinary and the ordinary rays of a single wave. Secondly, the present invention employs a unique combination of steps and means. Prior art is referenced to illustrate at least one teaching of each step and is not intended to limit the methods by which each step may be performed. The method and apparatus claims of this invention represent unique combinations that are not taught, motivated or suggested by the prior art.

Although a particular embodiment and form of the system has been illustrated, it is apparent that various modifications and embodiments of the system may be made by those skilled in the art without departing from the scope and spirit of the foregoing disclosure. Accordingly, the scope of the system should be limited only by the claims appended hereto.

I claim:

1. A method for measuring the density of a substance which is at least partially transparent to electromagnetic waves, which comprises the following steps in the order named:

supplying a source of at least one electromagnetic wave;

colliminating from the providing source the electromagnetic wave;

projecting at a known angle of incidence the wave through a desired area of a substance;

directing the wave through a linear polarizer;

encoding the wave by passing the wave through a device which encodes the angle of incidence of the wave upon the device as a phase shift between the ordinary and extraordinary components of the wave;

measuring the ordinary and the extraordinary components of the wave;

calculating the phase shift represented by the difference in the ordinary and extraordinary components;

converting the phase shift into a related density variation; and displaying the density variation in a manner suitable for the current application.

2. The method of claim 1, wherein the steps are performed with sufficient speed to generate a real-time display of the variations in densities within the substance.

3. The method of claim 2, wherein a multitude of waves are used to generate a display of density variations over a desired area of interest and at a desired degree of resolution.

4. The method of claim 3, wherein the steps are performed repeatedly at specified time intervals to generate a representation of the variations in densities within the substance as they vary over time.

5. The method of claim 2, wherein the steps are performed repeatedly at specified time intervals to generate a representation of the variations in densities within the substance as they vary over time.

6. The method of claim 1, wherein a multitude of waves are used to generate a display of density variations over a desired area of interest and at a desired degree of resolution.

7. The method of claim 6, wherein the steps are performed repeatedly at specified time intervals to generate a representation of the variations in densities within the substance as they vary over time.

8. The method of claim 1, wherein the steps are performed repeatedly at specified time intervals to generate a representation of the variations in densities within the substance as they vary over time.

9. A system for measuring the density of a substance which is at least partially transparent to electromagnetic waves, which comprises:

means for supplying a source of at least one electromagnetic wave;

means for colliminating the electromagnetic wave from and located in proximity to the source;

means for projecting at a known angle of incidence the colliminated wave though a desired area of a substance located in the path of the wave directly after the colliminater;

means for re-colliminating the wave located in the path of the wave directly after the substance;

means for directing the wave through a linear polarizer located in the path of the wave directly after the re-colliminating means;

means for encoding the angle of incidence of the wave upon the encoding means as a phase shift between the ordinary and extraordinary components of the wave located in the path of the wave directly after the directing means;

means for measuring the ordinary and the extraordinary components of the wave positioned in the path of the wave directly after the encoding means;

means for calculating the phase shift represented by the difference in the ordinary and extraordinary components;

means for transferring the measurements from the measuring means to the calculating means providing a connection between those two means;

means for converting the phase shift into a related density variation;

means for conveying the phase shift calculation from the calculating means to the converting means providing a connection between those two means;

means for displaying the density variation in a manner suitable for the current application; and means for transmitting the density variation from the converting means to the displaying means providing a connection between those two means.

10. The system of claim 9, wherein the means and structure employed allow sufficient speed to generate a real-time display of the variations in densities within the substance.

11. The system of claim 10, wherein the providing means furnishes a multitude of waves that are processed by the apparatus to generate a display of density variations over a desired area of interest and at a desired degree of resolution.

12. The system of claim 11, wherein the apparatus operates repeatedly at specified time intervals to generate a representation of the variations in densities within the substance as they vary over time.

13. The system of claim 10, wherein the apparatus operates repeatedly at specified time intervals to generate a representation of the variations in densities within the substance as they vary over time.

14. The system of claim 9, wherein the providing means furnishes a multitude of waves that are processed by the apparatus to generate a display of density variations over a desired area of interest and at a desired degree of resolution.

15. The system of claim 14, wherein the apparatus operates repeatedly at specified time intervals to generate a representation of the variations in densities within the substance as they vary over time.

16. The system of claim 9, wherein the apparatus operates repeatedly at specified time intervals to generate a representation of the variations in densities within the substance as they vary over time.

17. The system of claim 9, wherein the means for encoding is a phase shift assembly.

18. The system of claim 17, wherein the means and structure employed allow sufficient speed to generate a real-time display of the variations in densities within the substance.

19. The system of claim 18, wherein the providing means furnishes a multitude of waves that are processed by the apparatus to generate a display of density variations over a desired area of interest and at a desired degree of resolution.

20. The system of claim 19, wherein the apparatus operates repeatedly at specified time intervals to generate a representation of the variations in densities within the substance as they vary over time.

21. The system of claim 18, wherein the apparatus operates repeatedly at specified time intervals to generate a representation of the variations in densities within the substance as they vary over time.

22. The system of claim 17, wherein the providing means furnishes a multitude of waves that are processed by the apparatus to generate a display of density variations over a desired area of interest and at a desired degree of resolution.

23. The system of claim 22, wherein the apparatus operates repeatedly at specified time intervals to generate a representation of the variations in densities within the substance as they vary over time.

24. The system of claim 17, wherein the apparatus operates repeatedly at specified time intervals to generate a representation of the variations in densities within the substance as they vary over time.

* * * * *